United States Patent [19]

Lyon et al.

[11] 4,115,313

[45] Sep. 19, 1978

[54] BILE ACID EMULSIONS

[76] Inventors: Irving Lyon; Harriette Lyon, both of 415 N. Orange Grove Ave., Apt. 10, Los Angeles, Calif. 90036

[21] Appl. No.: 657,225

[22] Filed: Feb. 11, 1976

Related U.S. Application Data

[63] Continuation-in-part of Ser. No. 513,069, Oct. 8, 1974, abandoned.

[51] Int. Cl.² .............................................. B01J 13/00
[52] U.S. Cl. ........................................ 252/309; 8/86; 44/51; 71/64 C; 210/DIG. 27; 252/8.57; 252/49.5; 252/117; 252/132; 252/135; 252/312; 252/356; 252/DIG. 6; 252/DIG. 10; 424/57; 424/61; 424/64; 424/70; 424/71; 424/73; 424/164; 424/168; 424/172; 424/365; 424/DIG. 4; 426/62; 426/556; 426/562; 426/605; 426/614; 426/621; 426/651; 426/662; 426/811; 426/659
[58] Field of Search .................................. 424/49–52, 424/168, 172; 252/309, 312, 356

[56] References Cited

U.S. PATENT DOCUMENTS

| | | | |
|---|---|---|---|
| 1,773,123 | 8/1930 | Sullivan, Jr. .................. | 252/312 X |
| 1,973,991 | 9/1934 | McKesson et al. ............ | 252/311.5 |
| 2,052,026 | 8/1936 | Harris ............................ | 252/309 X |
| 2,216,485 | 10/1940 | Brandt ........................... | 252/312 X |
| 2,628,930 | 2/1953 | Zentner ......................... | 252/356 X |
| 3,346,494 | 10/1967 | Robbins et al. ................ | 252/312 X |
| 3,505,074 | 4/1970 | Pardun .......................... | 252/312 X |
| 3,926,840 | 12/1975 | Wendler et al. ............... | 252/356 |

*Primary Examiner*—Richard D. Lovering
*Attorney, Agent, or Firm*—Blakely, Sokoloff, Taylor & Zafman

[57] ABSTRACT

The invention is directed to emulsion compositions of, or including, bile acids, their conjugates, lower alcohol esters or salts of said acids or conjugates; water to effect solution of one or more of said defined bile acids; and at least one of: glycerides; phospholipids; fatty acids, amino fatty acids, or fatty acid amides; and steroids. Illustrative are sodium taurocholate, glyceryl monooleate, soy lecithin, oleic acid and cholesterol acetate. The emulsion compositions in conjunction with oil and/or water phase(s) can be controlled to give an emulsion product which is substantially stable water/oil type or oil/water type, or metastable mixture of water/oil and oil/water types. The emulsion product has utility in many fields such as cosmetics, dentifrices, food products, cleaners, lubricants, agricultural chemicals, etc; The emulsion composition itself has utility in many of these fields.

9 Claims, No Drawings

BILE ACID EMULSIONS

Cross-reference to Earlier Applications

This application is a continuation-in-part of our copending United States Pat. application Ser. No. 513,069, filed Oct. 8, 1974 now abandoned. This application and Ser. No. 513,069, now abandoned, are entitled to the date of our corresponding Denmark application Ser. No. 5180/74, filed Oct. 2, 1974.

A great variety of products depend for their activity on a stable state of emulsion. These products will generally be of various types, i.e., both oil-in-water and water-in-oil emulsions. The products as such may be free flowing viscous fluids, gels or even semi-solid substances which carry out their activity through surface contact, spreading, penetration and absorption.

The products would comprise articles used within the cleaning field, such as, cleaners, disinfectants and sterilizants, both for domestic and commercial as well as for industrial use, including also purification of crude oil and crude oil products, for instance in lubricants, particularly such as are desired to combine a lubricating and a cleansing effect. Other products would be medicaments and pharmaceuticals, specifically all kinds of products based on emulsions. This would include both products for external and topical use as well as those designed for internal use. Additional products would be those intended for use in the cosmetic field, particularly emulsion based cosmetics and preparations for mouth and vaginal hygiene. Also various kinds of foods may be included in particular those normally served in various sauces formulated as oil-in-water or water-in-oil emulsions, and also gravies, mayonaise, salad dressings and the like.

It is the object of the invention to improve the effectiveness and performance of such products by adding agents of natural origin which in very small concentrations produce and stabilize the micellar structures of the products and to provide agents for this purpose which also themselves possess advantageous micellar properties.

It is known in the art (see for instance A. White, P. Handler and E. L. Smith: "Principles of Biochemistry," McGraw-Hill Book Company, New York-Toronto-London) that the salts of conjugated bile acids are water soluble and are powerful detergents.

According to this invention it has now been found that bile acids and their conjugates, and the salts thereof produce or enhance several desirable chemical and physical properties such as adhesive and cohesive properties, detergent activity, effective lowering of surface tension, ability to suspend particles of dirt and other surfactant properties when incorporated in various products as specified above, even in very low concentrations, and that these properties will be further enhanced by the additional incorporation of one or more substances selected from among mono- and/or diglycerides, phospholipids, fatty acids and/or amino fatty acids and/or fatty acid amides, fats, and steroids.

Accordingly, the method of the invention is characterized by incorporating into the products bile acids of their derivatives, optionally together with one or more additional substances selected from among mono- and/or diglycerides, phospholipids, fatty acids and/or amino fatty acids and/or fatty acid amides, fats and steroids.

The invention also relates to an agent which is characterized in that it comprises bile acids or their derivatives, optionally in combination with one or more substances selected from among mono- and/or diglycerides, phospholipids, fatty acids and/or amino fatty acids and or fatty acid amides, fats, and steroids.

The bile acids include mainly cholic acid, deoxycholic acid, chenodeoxycholic and lithocholic acid and these acids in conjugated form combined with either glycine or taurine to form glycocholic acid, taurocholic acid etc. The bile acids and the conjugated acids can be used also in the form of their salts, particularly in the sodium salt form. In addition there is the possibility of using the acids in their ester forms in which the carboxyl group will be esterified with methanol or ethanol or other lower alcohols. Other derivatives that might be useful would include those in which the 3-hydroxy group in the A ring is combined with sugars to form glycosides, with uronic acids to form uronides or reacted to form sulfates, phenolates etc. The salts of the acids, especially those that are conjugated or reacted with various substances at the 3-hydroxy groups as mentioned above, have the advantage of being water soluble to varying degrees and are capable of exerting a powerful detergent action.

The mono- and/or diglycerides include $\alpha$- and/or $\beta$-monoglycerides and $\alpha,\alpha'$ — and/or $\alpha,\beta$ - diglycerides. The preferred glycerides are derived from mono-, di- , tri-, and/or polybasic carboxylic acids, among them the saturated and unsaturated fatty acids such as the $C_{12}$ to $C_{22}$ acids, inclusive. Examples of the preferred fatty acids are palmitic, palmitoleic, stearic, oleic, linoleic and linolenic.

The phospholipids include glycerol esters containing $\alpha$- or $\beta$- phosphoric acid, preferably mono- , di- , tri- and/or polybasic carboxylic acid diesters of glycerophosphate, and a hydroxy-containing compound combined in an ester link with the phosphate group. Choline, ethanolamine, inositol and serine are examples of such hydroxy-containing compounds found in natural phospholipids. Illustrative of the preferred phospholipids are lecithin and $\alpha$- or $\beta$- cephalin.

The fatty acids, amino fatty acids and fatty acid amides include or are derived from saturated and unsaturated fatty acids such as the $C_{12}$ to $C_{22}$ acids, inclusive. Examples of the preferred fatty acids are palmitic, palmitoleic, stearic, oleic, linoleic and linolenic. The term "amino fatty acids" is intended to include N- substituted amino fatty acids. In like manner, the term "fatty acid amides" is intended to include N-substituted fatty acid amides. Illustrative substituents in the N- substituted amino fatty acids and N- substituted fatty acid amides are alkyl and particularly lower alkyl such as methyl and ethyl.

The fats include the natural occurring triglycerides containing saturated and unsaturated fatty acids such as the $C_{12}$ to $C_{22}$ acids, inclusive. Examples of the preferred fatty acids in the triglycerides are palmitic, palmitoleic, stearic, oleic, linoleic and linolenic.

The steroids include plant and/or animal sterols and their esters. Illustrative of the animal sterols are cholesterol, 7- dehydrocholesterol and lanosterol. Illustrative of the vegetable sterols are phytosterol, ergosterol, sitosterol and stigmasterol.

Wherever possible there are many advantages in using natural substances produced by plants, animals, bacteria and fungi. Such substances have a minimal tendency to affect the surroundings owing to their easy biological disintegration, miscibility with water, solubility etc. Another advantage of natural substances is that they are active under relatively mild conditions with respect to temperature, pH, salt concentration etc., conditions which are typcial of the internal environments of living things and of the external environments compatible with their existence. This means that compositions containing natural substances can be prepared without requiring extreme physical and chemical conditions and the products containing natural substances will be more likely to be effective under ordinary circumstances of use and less likely to require special conditions to be effective. Similar considerations suggest that special storage facilities and/or storage conditions will not be required to preserve the stability of products containing natural substances.

Bile acids and their derivatives are natural substances which are present in the bile of a number of animals including humans and are produced by some microorganisms and plants. As mentioned above, they have been found to possess a number of desirable activities and they have proved to be effective in very low concentrations, viz. millimoles or even micromoles per liter rather than moles per liter, that is parts per million (ppm) and parts per billion (ppb) instead of parts per thousand (promille) or higher concentrations.

The concentration of the bile acids or their derivatives and of each of the one or more substances selected from among mono- and/or diglycerides, phospholipids, fatty acids and/or amino fatty acids and/or fatty acid amides, fats, and steroids which may optionally be present in the agent will typically be about 10 to 250 millimolar and preferably about 10 to 50 millimolar, particularly for the type of applications exemplified herein. Also, the concentration of the agent in the product will typically be about 0.5 to 100 parts per million (ppm) and preferably about 0.5 to 10 parts per million, particularly for the type of products exemplified herein. It should be understood, however, that the exact concentrations employed will depend on many factors including the product with which the agent is to be used and that the ranges specified are merely illustrative.

A practical consequence and advantage of incorporating such substances in a number of commercial products is that the same effectiveness will be obtained at lower cost or a higher effectiveness at the same or but slightly increased cost as compared with existing products.

It was found, as already mentioned, that the effect of incorporating bile acids or their derivatives can be further increased incorporating together with the bile acids one or more substances selected from among mono- and/or diglycerides, phospholipids, fatty acids and/or amino fatty acids and/or fatty acid amides, fats, and steroids. All these components are natural substances which are actually present in the human body. A series of tests with various compositions of these components have shown that they are active in lowering surface and interfacial tension and the apparent viscosity of oil to a considerable extent. Moreover, the resultant emulsions may be directed toward oil-in-water or water-in-oil type, dependent on the components of the composition, their relative concentrations and the volume ratio of oil to water. The tests also showed clearly that agents with several components tend to be more effective so that, for instance, those comprised of 4 or 5 components are more effective than those with fewer components. Moreover, the effect of the components in the said agents is not merely additive; they exhibit clearly a considerable synergistic effect. Besides, the activity of the said agents is clear even where the concentrations of the individual components are within the millimolar range.

Following the basic experiments with simplified agents according to the invention a number of possible applications of 4-component agents comprising a combination of a bile acid or a derivative thereof, a mono- and/or diglyceride, a phospholipid and a fatty acid were tested and also 5-component agents to which was further added a sterol or ester thereof. The tests include the application of the agents in cosmetic preparations (for hair, skin, nails and as deodorants), in preparations for oral hygiene, topical medicaments (applicable at a great number of dermatological conditions), foods (bakery products, meat products, cheese and other dairy produce), cleansing and polishing agents and dyes. These applications are illustrated by the subsequent examples. In the said tests a number of surprising results were observed which could not be predicted from a knowledge of the chemical structures of the employed compounds:

1. When used for general cleaning and hygiene:
   a. the agents cause fibers and hair to ball up as if an antistatic effect is exerted;
   b. the agents remove tartar effectively from the teeth and prevent accumulation of bacteria in cavities;
   c. after addition of the agents to an ordinary shampoo many more suds are created, whereby the cleaning effect of the shampoo is increased;
   d. by rinsing the hair with these agents the hair is left glossy, but not oily, free of fly-away and with greater body; this would imply similar benefits when using the agents in cleaning and conditioning of wool, especially in industries;
   e. when used alone or in soap the agents soften the skin by moisturizing it with an obvious emollient effect besides which they have a marked deodorant effect which is sufficient to obviate the use of commercial deodorants when the preparations are used daily.

2. When used in food:
   a. the agents solubilize the collagen in meat and act as an effective binder, so that the addition of the agents to, for instance, minced meat produce an end product that can be cut as if it were a whole piece of meat;
   b. in bread-making the agents make the dough easier and faster to knead, distribute the yeast or other leavening agents and other ingredients better and more homogeneously in the dough so that a more tasty and well shaped loaf which also toast faster and more evenly is obtained with less yeast, less oil and less spice;
   c. the use of the agents in food generally increase their taste and aroma, which appear to be associated with their ability to "strip" the taste buds to enable them to response more fully to tastes;
   d. the agents increase the digestibility of foods so that the addition of the agents to foods with a high content of fat or spice prevent or highly reduce heartburn and flatulence;
   e. a few drops of the agents on a frying pan prevent the food from sticking even in the absence of fat or oil, besides which the cleaning of dishes and pans is highly facilitated where the agents have been added to the food;

f. the addition of the agents to bread prevent or inhibit the development of mold on the bread.

3. Other surprising results with possible significance for cosmetic, medicaments and in agriculture:

a. when lipstick is smeared on the skin previously treated with agents according to the invention it begins to disappear within a few minutes; after 1 hour the lipstick in the treated region has penetrated substantially into the skin, whereas this does not happen in untreated areas;

b. employed in connection with shaving, the agents exhibit a marked haemostatic effect, particularly in the case of superificial capillary bleeding, which may occur during shaving;

c. the agents have a solubilizing effect on mucous such as may accumulate in the respiratory system when one has a cold;

d. in tests with the sprouting of soybeans it was found that the agents hasten the splitting of the seed covering and the emergence of the hypocotyl.

From the effects specified above under 3 a–c together with the general effect of preventing or impeding the growth of various microorganisms (for instance in the mouth, on the body and in bread, as mentioned above) it may be assumed that advantageous results will be obtained by using the agents in topical medicaments, anticatarrhal and sinus preparations as well as in medicine, bactericides and in the veterinary field, including artificial insemination. The last mentioned effect under 3d indicates a possible application in agriculture and hydroponics.

Although these agents, consisting of bile acids or derivatives thereof and preferably a plurality of the specified components, cover a wide field of possible application it is important to understand that they all depend on a few basic, simple properties. Most of the components are in varying degrees soluble in both oil and water and will, when added to products based on oil-in-water and water-in-oil emulsions, produce and stabilize micellar structures. These kinds of structures in an emulsion permit a more intimate contact between the emulsion and surfces whether they are found in living organisms, such as membranes, or in inanimate things of organic or inorganic nature, and whether they are penetrable or impenetrable. Under such conditions of increased contact the transfer and deposition of emulsion components must be expected to be facilitated, especially of micellar components. If the surface is penetrable, deposition may be followed by the penetration of the component into the surface and possibly by absorption. This may require additional components to act as carrier or medium for the primary components. Obviously the movement and transfer in the opposite direction, from the surface into the micell, can be expected to be facilitated in a similar manner.

Sometimes the agents according to the invention may tend to separate. In that case a protective colloid selected from among proteins and polysaccharides can be added in an amount of maximum 0.4% weight/volume. As suitable protective colloids for the agents according to the invention may be mentioned, for instance, gelatin, agar-agar, lactalbumin and pectin. It was found that generally concentrations exceeding 0.4% of the protective colloids woule have no stabilizing effect and that much higher concentrations would in fact cause separation of the emulsion. The proteins appear to be more effective than the polysaccharides, and the best results were obtained by the use of gelatin.

The presence of a bile acid or a bile acid derivative in the agents according to the invention is necessary for their stability. This is due to the ability of the bile acid and their derivatives to induce and stabilize micella structures in the formed emulsions and to their mutua solubility in oil and water. The combination of these two properties makes bile acids or derivatives thereo the ideal and perhaps necessary component to start witl in the preparation of agents according to the inventior which comprise more than two components. If the agents are to be obtained in the form of a stable emul sion, the sequence in which the components are added is in fact of great importance. According to the inventior agents comprising more than two components are therefore prepared by first mixing the components which are mutually soluble in oil and water and then adding the components which are either substantially soluble in oil or substantially soluble in water and mixing thoroughly.

As a practical example mono- and/or diglycerides (technical grade) were mixed thoroughly with powdered sodium taurocholate (technical grade) by mechanical stirring to form a smooth paste. Under continued stirring may be added phospholipids (for instance from soy) solubilized in a minimal volume of ethanol. After thorough mixing of these components, oil soluble substances such as triglycerides (fats), fatty acids and steroids and water soluble substances such as sterol esters may be admixed in practically arbitrary sequence. Where the agents require protective colloids for stabilization those components may conveniently be added after the addition of the phospholipids. The preparation may be illustrated by the following diagram.

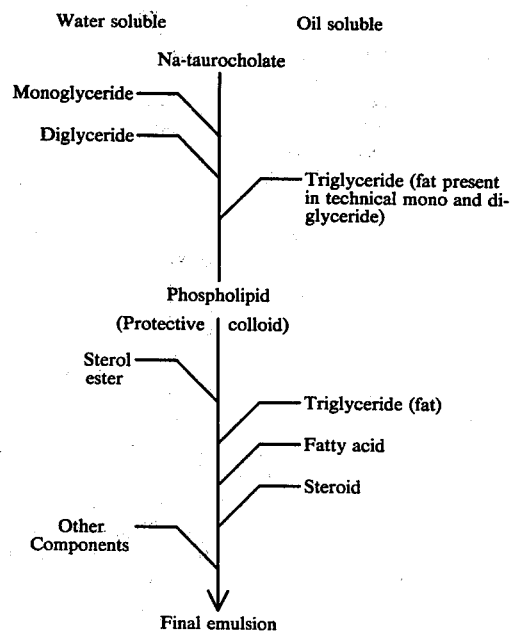

It should be mentioned that technical Na-taurocholate (for instance from ox bile) contains varying amounts of sodium salts of the glycine and taurine conjugates of the bile acids. Technical glyceryl monooleate contains approximately equal amounts of mono and diglyceride, a small amount of triglyceride and a medium amount of free glycerol. Soy lecithin is a variable mixture of glycerophophatides containing a preponderant amount of choline and also ethanolamine, serine and possible inositol. In the following embodiments of the emulsion composition, the soy lecithin was used in the form of a solution in a minimal amount of ethanol with an addition of water to provide a stock solution having a concentration of 1 g of lecithin per 5 ml of solution

EXAMPLES OF VARIOUS UTILITIES OF CERTAIN EMULSION COMPOSITIONS

Several embodiments of the emulsion composition of the invention were prepared by techniques as set forth hereinafter. The relative molar proportions of each component, except the water, present in each embodiment are set forth in the following Table 1. In the examples of utility, the specific embodiment is referred to by its molar proportions, e.g., 1313.

Table 1

| Component | Molar Proportion | | | | |
|---|---|---|---|---|---|
| Sodium taurocholate, technical grade | 1 | 1 | 1 | 1 | 1 |
| Glyceryl monooleate, technical grade | 3 | 1 | 1 | 1 | 3 |
| Soy Lecithin | 1 | 3 | 3 | 1 | 3 |
| Oleic acid | 3 | 1 | 1 | 3 | 3 |
| Cholesterol Acetate | 0 | 1 | 3 | 3 | 1 |

EXAMPLE I

Salad Dressing

A salad consisting of lettuce, tomato, cucumber, olives, cooked egg, beans, and small fish balls was divided into two portions. A dress was made of water, vingear, oil, salt, pepper and sugar; the dressing was divided into two portions. Each salad portion was between one-fourth and one-third of a measuring cup.

One portion of the dressing was left in the as prepared condition, that is, nothing further was added to it. 1313. Herein a drop is to be understood as a free falling body from an ordinary eyedropper; it has been observed that 20 drops equal 1 milliliter -ml-).

The 1313 treated dressing tasted sweeter and at the same time more vinegary, as though the taste had been sharpened. It was smooth, the oil droplets were hardly visible, compared with the untreated dressing. More importantly, the salad portion mixed with the 1313 treated dressing clearly tasted better than the salad portion mixed with the untreated dressing.

EXAMPLE II

Cooky and Bread Baking

A dry mixture was made from 180 ml flour, 180 ml oatmeal, 1 teaspoon baking powder, ½ teaspoon powdered nutmeg, and a sprinkle of salt and cinnamon.

A liquid mix was made of 180 ml milk, 1 whole egg, 1 teaspoon of almond essence; 5 drops of agent 1313 was then added and the mixture stirred. The mixture thickned quickly and became smooth; the egg white seemed to dissolve immediately after the agent 1313 was added.

The liquid and dry mixtures were then combined. The batter was almost immediately smoother than it is when no agent was added.

4 drops of agent 1313 were wiped onto one-half of an aluminum cooky sheet; the other one-half was left untreated. The batter was dropped onto the sheet in amounts to form the desired size cooky. The batter was baked for 10 minutes in a 260° C oven.

After the agent was added, it was observed that the batter bubbled visibly very soon after the addition, as though the baking powder had been activated. Also, it was observed that the batter distributed itself very evenly over the sheet about the point where the addition had been made. Also it was observed that the baked cookies had uniformly distributed, uniform sized holes.

The entire sheet cleaned easily with only water and a brush. This indicates that the agent 1313 addition facilitates cleaning whether it is applied to the sheet directly before baking or is merely present in the batter to be baked on the untreated sheet.

EXAMPLE III

White Bread

Two identical mixtures were made of: 180 ml warm milk; 25 g yeast; 1 teaspoon (tsp) of salt; 2 tablespoons (tbs) of brown sugar; 90 ml water, and 10 ml sunflower oil.

25 drops of agent 1313 were added to one mixture; the other was left as is. Each of these mixtures was added to 500 g of white flour and kneaded until elastic.

Two aluminum baking pans were coated on one-half of the inner surfaces with agent 1313.

The kneaded loaves were allowed to rise and then punched down. These were then put into the pans and allowed to rise a second time. Then the bread dough in the pans was baked at 250° C. for 25 minutes.

It was observed that: Both the 1313 containing loaf and the untreated loaf came out of the pans easily. Both had about the same texture and sliced the same way. However, the untreated loaf of bread had a flat taste and seemed to lack salt — the same amount was in both loaves. The 1313 treated bread had better taste than the untreated bread; and also it had a distinctive flavor.

Slices from each loaf were wrapped in plastic wrap and put on a shelf to observe the growth of mold. Mold eventually was observed on all slices, but it, i.e., the mold was considerably less, about one-third or less, on the 1313 treated bread slices.

EXAMPLE IV

Yeast Bread

To 360 ml of heated milk, there were added 4 tbp of brown sugar, 1 tsp of salt, and 2 tbp of sunflower oil; the mixture was cooled to lukewarm. The milk mixture was divided into 2 equal portions and to each portion was added 12.5 g of yeast.

25 drops of agent 1313 were added to one portion. Then each portion was added to 500 g of white flour in separate bowls. The mixtures were kneaded separately and allowed to rise to double bulk. Each mixture was punched down and allowed to rise a second time in a baking pan. Then the loaves were baked at 250° C for 45 minutes.

It was observed that: The oil droplets in the milk mixture containing the agent 1313 were much smaller and well dispersed throughout the mixture, than in the untreated mixture. The dough containing the agent 1313 kneaded faster and more easily than the untreated dough. The dough with the agent was able to take up a little more flour than the untreated dough. The dough with the agent rose more evenly both times, noticeably so, than the untreated dough. Also the treated dough distributed easily over the pan and was much more elastic than the untreated dough. The treated loaf browned sooner, looked done sooner, and more evenly then the untreated loaf. The final color of the treated loaf was noticeably darker brown on top. The treated loaf gave the impression of being lighter, although both loaves contained the same amount of ingredients. When sliced, the treated bread had more air holes than the untreated bread. On toasting: the treated bread toasted faster and all the way through the slice. However, the untreated bread slice did not brown and was soft in the center of the slice.

It is thought that the treated mixture made a more efficient use of the yeast than the untreated mixture.

EXAMPLE V

Yeast Bread

This Example was carried out identically to Example IV except that 50 drops of agent 1313 were added to the treated mixture, i.e., double the usage of Example IV.

It was observed that: The control loaf dough was difficult to knead compared to the treated dough. The dough without the agent absorbed less flour, leaving 26 tbps of flour, whereas the treated dough left only 13 tbps of flour. The treated dough rose more evenly and was more firm to the touch. The baked treated loaf did not brown as much on top. The treated bread seemed a bit more moist to the taste but left a slight aftertaste. Airholes appeared to be similar in both loaves. Untreated bread slice dried out faster and more unevenly than the treated bread.

EXAMPLE VI

Meat Loaf

About ¼ kg of ground beef, 1 tsp of salt and a sprinkle of pepper, 2 tbp of oatmeal, 2 tbp of "øllebrod"(a dish made from bread and beer), ½ tsp of cumin, and water was blended smoothly. Then 25 drops of agent 1313 was added and kneaded in. A loaf was shaped in oval form and allowed to stand for 15–30 minutes at room temperature. Then it was baked in a moderate oven for 30 minutes.

It was observed that: The warm meat loaf cut very smoothly as though it were a solid piece of meat. None of the individual pieces of meat typical of an ordinary meat loaf could be discerned. The meat loaf had an excellent taste. Left over loaf sliced even better when cold the next morning; also the taste seemed better. A slice fried in a pan with an egg on top looked, tasted, and felt like sliced meat.

EXAMPLE VII

Chocolate Fudge 4 drops of agent 11311 were spread on the interior of an enamel frying pan. One slice of sweet chocolate and 4 slices of little bitter chocolate were heated in the pan. To the soft chocolate was added 50 ml of milk mixed with agent 11311 and almond essence. The whole was blended together. The mixture was spooned onto 2 dishes, cooled and put into freezer, after putting hazel nuts on top.

It was observed that: the frozen mixes were thick and smooth, a surprising thickness like fudge, and had a good taste. A similar mixture which did not contain the agent gave mixes which were not as thick and smooth. It was noted that the milk containing the agent did not taste well before blending and heating with the chocolate. EXAMPLE VIII — AGENT AS SKIN CREAM

Cosmetic and Skin Treatment

Agent 11133 was spread evenly on face, elbows and heels of a woman.

It was observed that: The agent passes into the skin easily. The skin is smoothed and is less dry. In a few days the elbows were very smooth. Heels very tough but seem to respond a little.

EXAMPLE IX — LIPSTICK USE

Agent 11133 was applied to lower lip; the upper lip was not treated. Then lipstick was spread on both lips.

It was observed that: Much lipstick came off when the upper lip was blotted. Very little lipstick came off when the lower treated lip was blotted.

After 2 hours, it was observed that the lower treated lip was much lighter in color than after blotting. It was thought that the lipstick had passed into the lip tissue. This was confirmed by applying 2 smears of lipstick to areas on a forearm; one area had been treated with agent 11133 and the other area had not been treated. The agent allows the lipstick to penetrate into the skin.

EXAMPLE X — AGENT ON SKIN

Agent 13331 was rubbed on skin and penetrated almost immediately into the skin. Lipstick tests as carried out in Example IX showed a noticeable difference in skin penetration between treated and untreated areas.

EXAMPLE XI — SOAP CONTAINING AGENT 50 drops of agent 1313 were added to 50 g of soap. The body and hair of a woman was washed with the treated soap.

It was observed that: The skin was not dried out. However, the hair after washing was very oily and had to be washed out with shampoo, using much more shampoo than usual.

Further trial resulted in the observation that the treated soap effectively deodorized the axillae, genitalia, and feet for at least 24 hours.

This soap appears to be good for dry skin.

EXAMPLE XII — SOAP CONTAINING AGENT 50 drops of agent 11133 were added to 50 g. of soap. The body was washed with the treated soap.

It was observed that: The face was very dried out, even a bit more than with the commercial untreated soap. This treated soap appears to be good for oily skin. However, it was noticed that underarm odor was cut down very significantly for 24 hours.

EXAMPLE XIII — AGENT ON SKIN

Agent 11313 applied directly to the skin and nails, softens the skin and makes the nails less brittle. Repeated treatments for several weeks caused calluses to peel off leaving the skin below soft and pliable. Continued use prevented formation of new calluses.

EXAMPLE XIV — CORN REMOVAL FROM A TOE

A hard corn on a little toe was treated with agent 1313 for several days. On about the 7th day, the entire corn was easily picked out as a cone shaped body. It appears that even the root had been removed, after closer inspection of the toe.

EXAMPLE XV — HAIR RINSE

Hair Treatment 5 drops of agent 1313 were mixed with 180 ml of warm water. First, the hair was washed thoroughly with shampoo. Then the washed hair was rinsed with the agent containing water; the liquid was rubbed into the hair for about a minute and then rinsed out. The hair was dried well with a towel and thereafter with an electric comb hair dryer.

It was observed that: The hair seemed to have more body. The hair was very manageable on the second day which is a surprise. Usually hair must be washed or wetted to be manageable after one night's sleep upon it. The hair did not fly away but stayed in place better indoors and in windy weather outdoors.

EXAMPLE XVI — AGENT AS A HAIR CREAM

Agent 1313 was applied to a comb on both sides, 4 drops to each side. Before the comb became dry, the agent was combed through the hair.

It was startling to see the hair go into a desired configuration immediately. The hair tended to lose some body noticeably.

EXAMPLE XVII — HAIR RINSE 10 drops of agent 11133 were added to 2 tsp of water. After first washing the hair with a shampoo, the mixture was put on the hair, rubbed in well and left on about 10 minutes. Then the agent-water mixture was rinsed out and the hair was dried with a towel and then an electric comb hair dryer.

It was observed that: The hair had a good gloss. There was less body than obtained with agent 1313. There was no fly away; the hair stay in configuration indoors and outdoors, even on very windy days.

EXAMPLE XVIII — AGENT AS HAIR CREAM

Applying agent 13331 to a comb and using it in the manner of Example XVI, the hair was immediately much more manageable.

EXAMPLE XIX — AGENT AS HAIR CREAM

Agent 11313 has been used to condition hair in a manner similar to agents 1313 and 13331, supra.

EXAMPLE XX

Dentifrice

A dentifrice was prepared by mixing 50 ml of saturated solution of sodium silicate plus a pinch of sodium carbonate plus 6 drops of agent 1313. 1 drop of the dentifrice was used on a toothbrush daily for about one month.

During that time, it was observed that: the teeth glistened. The gums were pink and firm. Tartar between the teeth came out easily with dental floss.

A visit was made to a dentist, who observed: The teeth were tartar-free and the gums were pink and firm. One cavity was found; it was unusually free of decaying matter (clean) and required minimal drilling in preparation for a filling.

Approximately 14 months later, during which time the above dentifrice was not used, a dentist was visited in another country. This dentist observed that the teeth were covered with large amounts of tartar; however, all fillings and crowns were not loose and were free of holes.

EXAMPLE XXI

Shaving and Hair Trim

The face was washed thoroughly with soap and water. Agent 1313 was rubbed on one side of the face and on one sideburn around the ear and on half the back of the neck. Thereafter a shaving cream was applied, and the face and back of the neck shaved and the sideburns trimmed.

It was observed that: On the treated skin and hair, shaving and hair cutting was more easily done, with not only smooth cutting but also closer cutting, with less irritation of the skin. The treated sideburn was cut more evenly and the hair seemed to have less fly away.

EXAMPLE XXII — AGENT AS SHAVE CREAM

It has been observed that agent 11313 can be used instead of shaving soap or shaving cream. The agent appears to penetrate into the hair itself.

EXAMPLE XXIII — ON FURNITURE

Wood and Leather Treatment

Several drops of agent 1313 were spread on the surface of a wood table, leaving an untreated area.

It was observed that: The treated area had a soft glow. The treated area showed wood grain more prominently than the untreated area. Water was sprinkled on the table top; on the untreated area the water droplets did not spread out and retained the typical water drop on wood appearance; on the treated area the water droplets spread out and ran about assuming a flattened appearance.

EXAMPLE XXIV — LIQUID HOUSEHOLD CLEANER

A liquid cleaner was prepared by adding 6 drops of agent 1313 per 50 ml of saturated aqueous solution of sodium silicate plus a pinch of sodium carbonate. This mixture is diluted with water and applied with a cloth to the floor; the floor is allowed to dry.

It was observed that: No lint was left on the surface. The surface is glossy when dry. The dirt from the floor is suspended in the water solution.

EXAMPLE XXV — AGENT ON LEATHER SHOE

Several drops of agent 1313 were applied to a brown leather shoe, all the leather was not treated.

It was observed that: The agent spread very easily. The agent gave a glossy look to the leather and made it look better. Water ran off the treated surface, but did not run on the untreated surface. (This same 'running' effect was observed on glass, an impenetrable surface).

EXAMPLE XXVI — SNOWPROOFING LEATHER SHOES

One drop of agent 1313 was mixed with about 1/8 tsp of a commercial snowproof. The treated snowproof was spread on one shoe. Untreated snowproof was spread on another shoe.

It was observed that: Snowproof containing the agent was less sticky and spread more easily. It seemed to take less to cover the same area of shoe.

EXAMPLE XXVII

GLASS CLEANER

Eyeglasses were washed with water and dried with a rough towel. One lens was treated with a drop of 1313 on both sides; the excess was wiped off.

It was observed that: the treated lens picked up less dirt and fewer smudges in 2-3 days and could be wiped with a dry cloth and become clean again and remain this way. (It is beleived this indicates an anti-static effect of the agent.)

EXAMPLE XXVIII

DYEING CLOTH

A white cotton cloth, 10 cm square, was dyed in a solution of powdered "Dyalon" dye in 60 ml of water by boiling for 10 minutes. Then 17 drops of agent 1313 was added to the dye and another cloth was dyed by boiling for 10 minutes. The dyed cloths were hung to drip dry.

It was observed that: The treated cloth was much softer. The color of the two seemed the same but was richer and deeper in the treated cloth. The treated cloth wrinkled less than the untreated cloth.

One cloth dyed in the treated dye mixture had an aluminum chlorohydrol stripe painted down its center. Although the treated cloth with aluminum chlorohydrol had similar appearance and texture as the untreated cloth, the chlorohydrol odor permeated the entire treated cloth — having spread from the central stripe.

EXAMPLE XXIX

TOILET BOWL CLEANER

Agent 1313 and some liquid ammonia water were added to the water in a ceramic toilet bowl. The inside was washed with a bowl brush and wire wool. The cleaner dissolved (removed) most of the calcium carbonate deposit in the bowl.

EXAMPLE XXX

PASTEL CHALKS

Various colors of pastel chalks for painting were dipped in water containing agent 1313, one drop in a few drops of water. The same colors were dipped in untreated water. A stripe was painted with each chalk on a piece of paper.

It was observed that: The stripe with agent in the water dried faster and did not wet the paper as much on the back side. Next day it was noticed that particles of pastel were dissolved in the water treated with the agent. No such solution was evident in the untreated water.

The particles of pastel in the untreated water dissolved almost immediately after agent 1313 was added to that water.

EXAMPLE XXI

SOFTENING OF MUCOUS 10 drops of agent 1313 and coughed up mucous were mixed thoroughly in a test tube.

It was observed that: After 15 minutes the mucuous began to stick to the glass, suggesting that it was softening and that there was a spreading effect on the mucous. After standing overnight, the mucous seemed to have spread more evenly and more extensively over the glass surface. After 36 hours, the condition seemed to be about the same as at "overnight".

ADHERING TO PAN DURING FRYING OF FOOD

EXAMPLE XXXII — Pancakes

A pancake batter was made of flour, milk, baking powder, salt, and sugar. The pancakes were fried on an enamel pan coated lightly with 3–4 drops of agent 1313 on one half of the pan surface; the other half was not coated.

It was observed that: On the coated area the pancakes did not stick, had better texture and taste, and started rising sooner. On the uncoated area the pancakes stuck to the pan and had poor texture and taste.

EXAMPLE XXXIII — Egg

A mixture of egg and milk was fried on an enamel pan coated with 3–4 drops of agent 1313. The eggs stuck very little, less than if the pan had not been treated. The pan was washed easily with water and a brush.

EXAMPLE XXXIV — Egg

Example XXXIII was repeated with the same egg and milk proportion but this time without scrambling the egg mixture during the frying. The result was about the same as in Example XXXIII, i.e., slight sticking of eggs to the pan but easy washing of the pan.

EXAMPLE XXXV — Egg 3 drops of agent 1313 were applied to one half the surface of an enamel pan; the other half was untreated. A raw egg was dropped into the center of the pan.

The egg did stick to the untreated part of the pan, but did not stick to the treated part. There was a clear line across the bottom of the pan.

EXAMPLE XXXVI

COMPARISON OF OIL ON WATER WITH AND WITHOUT AGENT

1. Control Test

A 4 oz 'glass' glass about 10 cm high, about 5 cm outside diameter at the top and about 3 cm OD at the bottom was used in this example. Enough water was added to the glass to fill about one half its volume. Then a 10 ml amount of vegetable oil was placed on the water surface; the oil formed a layer above clear water.

The oil and water contents of the glass were mechanically agitated to effect "mixing."

It was observed that: The oil layer broke up into separate oil globules which, after a very brief period of several minutes, coalesce to reform a continuous oil layer on the water, over the entire surface thereof. This process can be seen more clearly by adding an oil soluble dye to the oil.

1.(a). The oil and water contents of the glass were again agitated to break the oil into globules. Before the globules had a chance to reform into a continuous oil layer, the mixture was poured from the glass onto the surface of a body of water held in a large diameter pan. The behavior of the contents of the pan was observed over the next 10–15 minutes.

It was observed that: Many of the oil globules coalesced to form a number of quite large oil areas, roughly circular, upon the surface of the water. There was no tendency for the oil drop areas to disperse or move toward the wall of the pan, showing little effective horizontal dispersal of the oil. There was no tendency of the oil to move down into the water beneath, showing a lack of vertical dispersion of the oil.

2. Test of an Embodiment of the Invention (a). This test 2.(a) was carried out as described in Test 1, supra, except that after the oil layer had been formed on the water in the glass, about 1 ml of agent 1313 was poured onto the oil.

It was observed that: The agent settled at the interface between the oil and the water. That is, the agent rested at the bottom surface of the oil upon the upper surface of the water. This suggests that some of the molecules of the agent are soluble in the oil above, and other molecules are soluble in the water below. The mutual solubility of some of the components of the agent in both the oil and in the water can bring water and oil into intimate contact with each other. This is required as a first step in the eventual emulsification of the oil and the water.

(b). The contents of the glass were mechanically agitated to form oil globules. It was observed that these oil globules were finer than the globules formed in the absence of agent and that these finer oil globules showed considerable resistance to coalescence and to reform a continuous oil layer.

(c). An agitated mixture was poured onto the surface of water in the large diameter pan used in Test 1.

It was observed that: The distribution pattern of the oil was very different from that of the control test 1. In this Test 2.(c), there was considerably less tendency of the oil globules to recoalesce (merge) into larger oil areas. Surprisingly, oil areas moved to the wall of the pan and around the periphery thereof to form a more or less continuous band of oil. It appeared that, if the wall of the pan were not present, the oil would have continued to move away from the center of the pan — possibly forming a monomolecular or at least very thin layer on the water. Moreover, there is a marked tendency of the oil to move vertically down into the water to form a rather significant 'layer' within the water below the oil layer areas on the water surface.

Conclusions drawn from this Example

These tests demonstrate that the agent exerts strong oil dispersing effects, resulting in both horizontal and vertical movement of the oil. Also, in the presence of the agent, significant amounts of oil are emulsified with water as shown by a milky, cloudy appearance of the water beneath the oil layer.

This movement of the oil and emulsification are facilitated by mechanical agitation, such as that which would be caused by wind and wave action in the ocean. It seems highly likely that these agents can be used effectively in the dispersion of mineral oil spilled at sea.

Other applications of these findings include: facilitation of movement of oil through pipelines; prevention and/or inhibition of formation of oil sludges, as well as sludge removal; the formation of smooth burning mixtures of oil and water for fuel injection in motor vehicles and other types of burner systems.

EXAMPLES OF EMULSIONS PRODUCED USING AGENT OF THE INVENTION

In the following, various agents of the invention were used in conjunction with oil, or oil and water and the results observed after vigorous agitation of the materials. Most of the work was carried out using test tubes having a 16 mm internal diameter; some work was carried out using a small jar having a 45 mm ID.

In addition to water, the following materials were used at one time or another:

| Material | Identification Code |
|---|---|
| Sodium taurocholate, Technical grade (537.7 MW) | TC |
| Glyceryl monooleate, Technical grade (534.8 MW) | MG |
| Soy Lecithin (785 MW) | PL |
| Olive oil | Oil |
| Sunflower oil | Oil |
| Oleic acid (282 MW) | FA |
| Cholesterol Acetate (428 MW) | CHOL |

The taurocholate was dissolved in water to provide 25 mg or 9.3 millimoles (mM) per 1 of solution. The olive oil had a viscosity of 80 centipoises at 20° C. Usually a slight amount of water soluble methyl orange dye was added to the TC solution to assist in determining the type of emulsion formed. In some instances an oil soluble blue dye was also present.

In the tests, the amounts of the agent components, i.e., TC, MG, PL, FA, CHOL, are always expressed in relative molar proportions. The normal "1" amount was 9.3 mM. However in some instances, the "1" amount was slightly lower or higher but the molar proportion of the components of the agent remained constant regardless of the absolute amount of each component present.

The oil/water (O/W) and water/oil (W/O) ratios are always set out as volume/volume.

Test A — Effect of TC alone

In this test, other tests, and examples, the amount of water, oil, and Agent are in ml.

| No. | 1 | 2 | 3 | 4 | 5 | 6 | 7 |
|---|---|---|---|---|---|---|---|
| Water | 0 | 0.65 | 1.15 | 1.5 | 1.85 | 2.35 | 3.0 |
| TC sol'n | 1.0 | 1.0 | 1.0 | 1.0 | 1.0 | 1.0 | 1.0 |
| oil | 4.0 | 3.35 | 2.85 | 2.5 | 2.15 | 1.65 | 1.0 |
| Emulsion type | W/O | W/O-O/W | O/W | O/W | O/W | O/W | O/W |
| Oil/Water present | 4.0 | 2.0 | 1.3 | 1.0 | 0.75 | 0.50 | 0.25 |

In this test A the water, TC solution and oil were added and then vigorously shaken.

Test B — Effect of TC alone

In this test the water and oil were vigorously shaken first then the TC solution added and the whole shaken again.

| No. | 1 | 2 | 3 | 4 | 5 | 6 | 7 |
|---|---|---|---|---|---|---|---|
| Water | 0.65 | 0.85 | 1.00 | 1.15 | 1.40 | 1.65 | 1.95 |
| oil | 3.35 | 3.15 | 3.00 | 2.85 | 2.60 | 2.35 | 2.05 |
| TC | 1.0 | 1.0 | 1.0 | 1.0 | 1.0 | 1.0 | 1.0 |
| Emulsion | W/O | W/O | W/O-O/W | O/W | O/W | O/W | O/W |
| Oil/Water present | 2.0 | 1.7 | 1.5 | 1.3 | 1.1 | 0.9 | 0.7 |

In this test the apparent viscosity of the oil in the emulsion was calculated and was found to be about 2 centipoises. This is an astounding decrease from the oil alone viscosity of 80 centipoises.

Test C — Effect of TC alone

In a test tube, 1 ml oil plus 1 ml TC solution and then water was added 0.5 ml at a time and the tube shaken after each water addition. The emulsion inverted from W/O type to O/W type at an oil/water present ratio of 0.33. The apparent viscosity of the oil was 9.9 centipoises. The surface to volume ratio was 0.23.

In another test tube, 4 ml oil plus 1 ml TC solution and then water addition as above. The emulsion inverted at an oil/water ratio of 0.67. Apparent oil viscosity was 2.2. Surface to volume ratio was 0.17.

In another test, the jar was used with 4 ml of oil and 1. ml of TC solution and water added as above. The emulsion inverted to O/W type at 1.33. The apparent viscosity of the oil was 1.8 and the surface to volume ratio was 0.91.

In another test a TC solution having 27.9 mM (triple that of the earlier tests) was tested as before in both test tube and in the jar. In this higher TC usage tests, the test tube and the jar gave essentially the same results, namely, an apparent oil viscosity of 2.6 centipoises at the inversion point of oil/water ratio of 1.6.

Test D — TC AND MG USED TOGETHER IN THE AGENT

In this test, the TC:MG molar proportion was 1:1, however the "TC solution" contained 27.9 mM of each material.

| No. | 1 | 2 | 3 | 4 | 5 | 6 | 7 |
|---|---|---|---|---|---|---|---|
| oil | 4.0 | 3.35 | 2.5 | 1.65 | 0.9 | 0.6 | 0.2 |
| Agent | 1.0 | 1.0 | 1.0 | 1.0 | 1.0 | 1.0 | 1.0 |
| Water | 0. | 0.65 | 1.5 | 2.35 | 3.1 | 3.4 | 3.8 |
| Emulsion | W/O | W/O | W/O | W/O | W/O-O/W | O/W | O/W |
| oil/water present | 4.0 | 2.0 | 1.0 | 0.5 | 0.22 | 0.14 | 0.04 |

A test at 1:1 proportion at 9.3 mM of each of TC and MG gave results very similar to the above test D.

It is striking how much more stable the W/O type emulsion is when the glyceride component is present along with TC in the agent, then when TC alone is present.

Test E — TC AND PL USED TOGETHER IN THE AGENT

In this test the TC:PL proportion was 1:1; however, 27.9 mM of each material was present in the agent.

| No. | 1 | 2 | 3 | 4 | 5 | 6 | 7 |
|---|---|---|---|---|---|---|---|
| Oil | 9.0 | 8.55 | 7.5 | 5.0 | 2.5 | 1.45 | 1.0 |
| Agent | 1.0 | 1.0 | 1.0 | 1.0 | 1.0 | 1.0 | 1.0 |
| Water | 0. | 0.45 | 1.5 | 4.0 | 6.5 | 7.55 | 8.0 |
| Emulsion | W/O-O/W | W/O-O/W | W/O-O/W | O/W | O/W | O/W | O/W |
| oil/water present | 9.0 | 5.9 | 3.0 | 1.0 | 0.33 | 0.17 | 0.11 |

The fact that the TC+PL is a better director toward the O/W type emulsion is almost dramatically shown by the metastable emulsions at high oil/water ratios. The TC+MG test D shows a direction toward the W/O type emulsion until low oil/water ratios.

TESTS ON TC, MG and PL USED TOGETHER IN THE AGENT

A series of tests were made with TC, MG, and PL together in the agent. Concentrations both at 9.3mM and 27.9mM were used. Methyl orange dye was present in the agent. The oil/water ratio was varied in various tests from 9:1 to 1:9.

In the following Table 2 are presented the results of these tests. The apparent viscosity of the oil at the inversion point was calculated and is shown. The emulsion type favored by the particular combination of components is shown. To complete the picture the number of emulsions definitely of that type is shown as well as the number of the other type and metastable emulsions, if any; this item is shown as "frequency" in the table.

Table 2

| Test F: Agent Proportion TC:MG:PL | Viscosity, Oil Centipoises | Emulsion Type Favored | Frequency |
|---|---|---|---|
| 1:1:1 | 4. | O/W | 4/3 |
| 1:1:3 | 4. | O/W | 4/3 |
| 1:3:1 | 20. | O/W | 5/2 |
| 1:3:3 | 2. | W/O | 4/3 |
| 3:1:1 | 2. | W/O | 4/3 |
| 3:1:3 | 6. | O/W | 4/3 |
| 3:3:1 | 2. | W/O | 4/3 |
| 3:3:3 | 2. | W/O | 4/3 |

The results in the table demonstrate the flexibility of the three component agent in terms of the types of emulsions which can be prepared, and in the viscosity of the oil present in the emulsion.

Test G (Experiment 13)

Experiment 13 shows a typical pattern of the emulsion types obtained in the W/O emulsion type favored experiments shown in Table 2 of Test F. In this test, the TC:MG:PL proportion was 1:3:3.

| No. | 1 | 2 | 3 | 4 | 5 | 6 | 7 |
|---|---|---|---|---|---|---|---|
| Oil | 9.0 | 8.55 | 7.50 | 6.65 | 5.0 | 3.35 | 2.0 |
| Agent | 1.0 | 1.0 | 1.0 | 1.0 | 1.0 | 1.0 | 1.0 |
| water | 0 | 0.45 | 1.50 | 2.35 | 4.0 | 5.65 | 7.0 |
| Emulsion | W/O | W/O-O/W | W/O-O/W | W/O-O/W | O/W | O/W | O/W |
| oil/water present | 9.0 | 5.9 | 3.0 | 2.0 | 1.0 | 0.5 | 0.25 |

TESTS ON TC, MG, PL AND FA USED TOGETHER IN THE AGENT

A series of tests were made with TC, MG, PL and FA together in the agent. In the following Table 3 the results of these tests are presented, where the columns have the same meaning as the columns in Table 2 — except for the Agent column.

Table 3

| Test H: Agent Proportion TC:MG:PL:FA | Viscosity, Oil Centipoises | Emulsion Type Favored | Frequency |
|---|---|---|---|
| 1:1:1:1 | 2. | W/O | 4/3 |
| 1:1:1:3 | 2. | W/O | 4/3 |
| 1:1:3:1 | 6. | O/W | 4/3 |
| 1:1:3:3 | 2. | W/O | 4/3 |
| 1:3:1:1 | 2. | W/O | 4/3 |
| 1:3:1:3 | 2. | W/O | 4/3 |
| 1:3:3:1 | 9. | O/W | 4.2 |
| 1:3:3:3 | 20. | O/W | 5/2 |
| 3:1:1:1 | 2. | W/O | 4/3 |
| 3:1:1:3 | 6. | O/W | 4/1 |
| 3:1:3:1 | 6. | O/W | 4/3 |
| 3:1:3:3 | 4 | W/O | 3/3 |
| 3:3:1:1 | 20. | O/W | 5/2 |
| 3:3:1:3 | 6. | O/W | 4/3 |
| 3:3:3:1 | 6 | O/W | 4/3 |
| 3:3:3:3 | 6 | O/W | 4/3 |

This series is interesting in that with the exceptions of the 1:3:3:1, the 3:1:1:3 and 3:1:3:3 agent containing systems, none of the agents formed metastable emulsion types. These 3 systems formed, respectively, 1, 2 and 1 metastable types.

Test J (Experiment 23)

Test J presents an experiment showing the sharp inversion point it is possible to obtain by adjustment of the components of this four component agent, namely, 1:3:1:3.

| No. | 1 | 2 | 3 | 4 | 5 | 6 | 7 |
|---|---|---|---|---|---|---|---|
| Oil | 9.0 | 8.55 | 7.5 | 6.65 | 5.0 | 3.35 | 2.0 |
| Agent | 1.0 | 1.0 | 1.0 | 1.0 | 1.0 | 1.0 | 1.0 |
| Water | 0 | 0.45 | 1.5 | 2.35 | 4.0 | 5.65 | 7.0 |
| Emulsion oil/water | W/O | W/O | W/O | W/O | O/W | O/W | O/W |
| present | 9.0 | 5.9 | 3.0 | 2.0 | 1.0 | 0.50 | 0.25 |

TESTS ON TC, MG, PL, FA AND CHOL USED TOGETHER IN THE AGENT

A series of tests were made with TC, MG, PL, FA and CHOL (cholesterol acetate) together in the agent. The following Table 4 contains the results where the molar proportion of TC was held to 1. Each composition had a frequency of 4/3 (*).

Table 4

| Test K: | | | |
|---|---|---|---|
| Agent Proportion TC:MG:PL:FA:CHOL | Viscosity, Oil Centipoises | Emulsion Type Favored | Frequency |
| 1:1:1:1:1 | 6 | O/W | 4/3 |
| 1:1:1:1:3 | 6 | O/W | * |
| 1:1:1:3:1 | 2 | W/O | * |
| 1:1:1:3:3 | 2 | W/O | * |
| 1:1:3:1:1 | 6 | O/W | * |
| 1:1:3:1:3 | 6 | O/W | * |
| 1:1:3:3:1 | 6 | O/W | * |
| 1:1:3:3:3 | 6 | O/W | * |
| 1:3:1:1:1 | 6 | O/W | * |
| 1:3:1:1:3 | 1.4 | W/O | * |
| 1:3:1:3:1 | 6 | O/W | * |
| 1:3:1:3:3 | 2 | W/O | * |
| 1:3:3:1:1 | 6 | O/W | * |
| 1:3:3:1:3 | 6 | O/W | * |
| 1:3:3:3:1 | 6 | O/W | * |
| 1:3:3:3:3 | 6 | O/W | * |

Test L: Another series of tests was made with the 5 components in the agent. The following Table 5 contains the results when the molar proportion of TC was held to 3.

Table 5

| Agent Proportion TC:MG:PL:FA:CHOL | Viscosity, Oil Centipoises | Emulsion Type Favored | Frequency |
|---|---|---|---|
| 3:1:1:1:1 | 6 | O/W | * |
| 3:1:1:1:3 | 6 | # | * |
| 3:1:1:3:1 | 6 | # | * |
| 3:1:1:3:3 | 6 | # | * |
| 3:1:3:1:1 | 6 | # | * |
| 3:1:3:1:3 | 2 | W/O | * |
| 3:1:3:3:1 | 6 | # | * |
| 3:1:3:3:3 | 6 | # | * |
| 3:3:1:1:1 | 6 | #* | |
| 3:3:1:1:3 | 19 | # | 5/2 |
| 3:3:1:3:1 | 6 | # | * |
| 3:3:1:3:3 | 6 | # | * |
| 3:3:3:1:1 | 6 | # | * |
| 3:3:3:1:3 | 6 | # | * |
| 3:3:3:3:1 | 6 | # | * |
| 3:3:3:3:3 | 6 | # | * |

Notes:
*equals frequency of 4/3
equals favored emulsion type of O/W

It is of interest in the 32 results reported in Tables 4 and 5 only one had a frequency different from 4/3 and that was the highest oil viscosity instance 3:3:1:1:3 where the frequency was 5/2 but the emulsion type favored was still O/W. Also, it is of interest that only five of the results had an emulsion type of W/O with all five results having a frequency of 4/3; these were the only instances where the apparent oil viscosity was about 2 or lower. Surprisingly not one of the 32 results showed even one situation of a metastable emulsion type. Also it was observed that an increase in TC amount in all four of the W/O emulsion types favored in Table 4 caused them to pass to the O/W favored type in Table 5. The one instance in which an O/W type in Table 4, namely, 1:1:3:1:3, changed to an W/O type in Table 5 appears to be suspect, even though these results were actually obtained.

Each of the 32 results reported in Tables 4 and 5 is distinguished by the stability of the emulsions formed and of the sharpness of the inversion point.

EXAMPLE XXXVII

DETERMINATION OF THE EFFECTS OF INDIVIDUAL AGENT COMPONENTS IN EMULSION FORMATION

Five 'glass' glasses were used in this example. Each glass was about 10 cm high and about 5 cm in diameter at the top with somewhat sloping sides. To each glass was added 4 oz of water and then 20 drops of safflower oil, containing 1 drop of oil soluble dye; two distinct layers were formed in each glass.

TC was prepared in water solution, 9.3 mM per ml of solution. Then a TC+MG in water mixture; then a TC+MG+PL in water mixture; then a TC+MG+PL+FA in water mixture, was prepared. Each of the symboled components was present in molar proportions based on the 9.3 mM of TC, so that the 4 symbol agent corresponded to the 1:3:1:3 agent of the earlier examples and tests.

The contents of each glass after 10 drops of the agent component had been added, as shown, is set forth in Table 6. The agent components are shown in molar proportion.

Table 6

| Glass No. | 1 | 2 | 3 | 4 | 5 |
|---|---|---|---|---|---|
| Water, oz. | 4 | 4 | 4 | 4 | 4 |
| Oil, drops | 20 | 20 | 20 | 20 | 20 |
| TC | 0 | 1 | 1 | 1 | 1 |
| MG | 0 | 0 | 3 | 3 | 3 |
| PL | 0 | 0 | 0 | 1 | 1 |
| FA | 0 | 0 | 0 | 0 | 3 |

Each glass was agitated by five swirls of a rod through the contents of the glass. It was observed that with the exception of glass No. 1, there was oil break-up and formation of cloudiness in the aqueous phase, which indicates emulsion formation. The extent of oil break-up and cloudiness was determined visually by inspection of the glasses after a short settling time; these observations are reported in Table 7 for each glass in a "most to least" order.

Table 7

| Oil Break-up Glass No. | Cloudiness in Aqueous Phase |
|---|---|
| 5 | 5 |
| 2 | 4 |
| 3 | 3 |
| 4 | 2 |
| 1 | 1 |

It is surprising that the order of oil break-up should be so different from the order for cloudiness formation. It is selfevident that the more components the better the ability to form emulsions.

EXAMPLE XXXVIII

STUDY OF THE PENETRATION OF LEATHER BY VARIOUS COMPOSITIONS

The compositions used in this example were the same as used or made up in Example XXXVII.

Method

One drop of oil was placed on raw shoe leather at four locations. The oil was allowed to penetrate the leather. Then one drop of water was placed on top of each drop of oil, i.e., at that location. Then one drop each of the respective compositions Glass No's. 2-5 was place on one of the oil locations. (Each oil location received only one composition having an agent component.) Water alone was used as a control at one location.

It was observed that after one additional drop of oil was placed on each of 5 spots: There was no effect on the water only control spot. There was slightly more spreading on the TC spot than on the water only spot. There was more spreading on the TC/MG and TC/MG/PL spots than on the TC spot. There was very marked, rapid spreading of the oil on the TC/MG/PL/PL spot.

Fifteen minutes later razor blade cuts were made through the center of each spot on the raw leather. The degree of penetration of the oil soluble dye was observed. The penetrations were ranked from most to least as follows: Most: Glass No. 5 (TC/MG/PL/FA); Next: Glasses No. 4(TC/MG/PL) and No. 3 (TC/MG); Next: Glass No. 2 (TC solution); least: the water spot control.

ILLUSTRATIVE EMBODIMENTS

1. Elemental sulfur has been used in medicine and there is set out an emulsion composition containing finely divided elemental sulfur which may be used as is or made a part of a salve or ointment. (a). TC solution is mixed with MG. (b). Micronized elemental sulfur is added and the materials mixed. (c). PL is then added and the materials mixed. (d). FA is then added and the materials mixed. (e) CHOL is an optional component. (f) Add the desired amount of water. The proposed final embodiment consists of approximately 1:3:1:3 agent plus 0.1-0.5 weight percent of sulfur. Depending upon the micronization of the sulfur the final product may be close to the feel of 1313 alone; or it might be slightly less smooth to the feel.

2. This embodiment which may be used in a shampoo for treatment of dandruff, such as Selson blue or Head & Shoulders shampoos, is the same as No. 1 above, except that selenium monosulfide may be used to replace the sulfur entirely or may be used in combination with sulfur. The total weight of selenium monosulfide and sulfur, if any, should be about the same as for the sulfur given in No. 1 above.

Thus having described the invention, what is claimed is:

1. An emulsion composition consisting essentially of:
   (1) bile acid member selected from the class consisting of bile acids, bile acid conjugates, lower alcohol esters of bile acids or bile acid conjugates, salts of bile acids or bile acid conjugates, and mixtures thereof;
   (2) water to effect solution of said bile acid member; and
   (3) at least one component selected from the cla consisting of:
      (a) glycerides of fatty acids having about 12-2 carbon atoms;
      (b) phospholipids selected from the group consis ing of (i) glycerol esters containing alpha or be phosphoric acid and (ii) a hydroxy-containir compound combined in an ester link with a pho phate group;
      (c) fatty acids, amino fatty acids, or fatty acid amide where said fatty acids have about 12-22 carbc atoms and said amino fatty acids and said fatty ac amides are derivable from fatty acids having abo 12-22 carbon atoms; and
      (d) steroids selected from the group consisting of ( animal sterols and (ii) vegetable sterols, where sai bile acid member and each of said (a), (b), (c) an (d) units of said component (3), when present, present in said emulsion composition in an amou between about 10 and 250 millimoles per liter ( said bile acid member-water solution, and whei the molar proportion of each of said componen 3a, 3b, 3c and 3d, when present, lies in the range ( about 0.3-3 moles per mole of said component (1 present.

2. The emulsion composition of claim 1 wherein sai conjugate is sodium taurocholate.

3. The emulsion composition of claim 1 wherein sai glyceride is glyceryl monooleate.

4. The emulsion composition of claim 1 wherein sai fatty acid is oleic acid.

5. The emulsion composition of claim 1 wherein sai phospholipid is soy lecithin.

6. The emulsion composition of claim 1 wherein sai steroid is cholesterol acetate.

7. The emulsion composition of claim 1 wherein stabilizing amount of protein or polysaccharide protec tive colloid is present.

8. An emulsion product that may be characterized a (1) substantially stable water-in-oil type, (2) substar tially stable oil-in-water type, or (3) mixed metastabl water-in-oil type and oil-in-water type,
   which emulsion product obtains its character froi the intermingling of (a) liquid oil, or (b) liquid o and water, and (c) emulsion composition as define in claim 1,
   the proportions of said liquid oil, said water, if an} and said emulsion composition, and the relativ proportions of bile acid member and each unit c said component (3), present, is controlled to obtai an emulsion product of the desired emulsion typ( 9. An emulsion composition consisting essentially o
   (1) sodium taurocholate,
   (2) water to effect solution of said taurocholate,
   (3) a mixture of glycerides, substantially the monc and di-oleates,
   (4) soy lecithin,
   (5) oleic acid,
      where said taurocholate, said glycerides, said lec thin, and said oleic acid are present in the mol; ratio of about 1:3:1:3 and each of said taurochc late, said glyceride mixture, said lecithin, an said oleic acid is present in said emulsion comp( sition in an amount between about 10 and 5 millimiles per liter of said taurocholate-wat( solution.

* * * * *